US007339165B2

United States Patent
Donaldson et al.

(10) Patent No.: US 7,339,165 B2
(45) Date of Patent: Mar. 4, 2008

(54) DUAL OUTLET PYROLYZER FOR BIOLOGICAL AGENT DETECTION SYSTEM

(75) Inventors: William S. Donaldson, LaVerne, CA (US); Richard K. Chun, Alhambra, CA (US)

(73) Assignee: Hamilton Sundstrand Corporation, Rockford, IL (US)

( * ) Notice: Subject to any disclaimer, the term of this patent is extended or adjusted under 35 U.S.C. 154(b) by 272 days.

(21) Appl. No.: 11/174,915

(22) Filed: Jul. 5, 2005

(65) Prior Publication Data

US 2006/0006327 A1 Jan. 12, 2006

Related U.S. Application Data

(60) Provisional application No. 60/586,663, filed on Jul. 9, 2004.

(51) Int. Cl.
*B01D 59/44* (2006.01)
(52) U.S. Cl. .............. 250/288; 250/284; 250/287; 250/286; 250/423 P; 250/293; 250/281; 250/282; 313/359.1; 219/121 P
(58) Field of Classification Search ............. None
See application file for complete search history.

(56) References Cited

U.S. PATENT DOCUMENTS

| 4,251,725 | A * | 2/1981 | Adkisson ............. 250/281 |
| 6,627,881 | B1 * | 9/2003 | Bertrand et al. ........ 250/288 |
| 7,057,168 | B2 * | 6/2006 | Miller et al. ............. 250/287 |
| 2005/0133716 | A1 * | 6/2005 | Miller et al. ............. 250/293 |

OTHER PUBLICATIONS

Harrington, Peter de B., Validation Using Sensitivity and Target Transform Factor Analyses of Neural Network Models for Classifying Bacteria from Mass Spectra, American Society for Mass Spectrometry, Oct. 11, 2001, Elsevier Science Inc.
Hendricker et al., Rapid Chemotaxonomy of Pathogenic Backterial Using in Situ Thermal Hydrolysis and Methylation as a Sample Preparation Step Coupled With a Field-portable Member-inlet Quadrupole Ion Trap Mass Spectrometer, International Journal of Mass Spectrometry, Nov. 3, 1998, Elsevier Science B.V.
Basile et al., Pathogenic Bacteria: Their Dectection and Differentiation by Rapid Lipid Profiling With Pyrolysis Mass Spectrometry, Trends in Analytical Chemistry, vol. 17 No. 2, 1998, Elsevier Science B.V.

* cited by examiner

*Primary Examiner*—Jack I. Berman
*Assistant Examiner*—Zia R. Hashmi
(74) *Attorney, Agent, or Firm*—Carlson, Gaskey & Olds

(57) ABSTRACT

A chemical biological detection system detects the presence of biological agents in the air. The system includes a pyrolyzer having an inlet through which air is drawn into the pyrolyzer and a pyrotube that collects a sample of particles extracted from the air. The pyrolyzer further includes an exhaust line that exhausts the air drawn into the pyrolyzer and a sample line that directs the gases eluted from the sample collected in the pyrotube to a mass spectrometer for sample identification. After the sample is collected in the pyrotube, the sample is analyzed. A small droplet of a methylating reagent is added to the sample. If the sample includes any biological agents, the methylating reagent derivatizes organic materials to make them more volatile. The sample is then pyrolyzed, and the eluted gas sample is drawn through the sample line and into the mass spectrometer for identification of any biological agents.

22 Claims, 2 Drawing Sheets

DUAL OUTLET PYROLYZER FOR BIOLOGICAL AGENT DETECTION SYSTEM

REFERENCE TO RELATED APPLICATIONS

This application claims priority to U.S. Provisional Patent Application No. 60/586,663 filed Jul. 9, 2004.

BACKGROUND OF THE INVENTION

The present invention relates generally to a dual outlet pyrolyzer used to detect biological agents present in the air.

A chemical biological mass spectrometer block II (CBM-SII) detects biological agents present in the air by employing a two step process. During sample collection, a first pump draws 1 liter of air per minute into a pyrolyzer through an inlet. The air drawn into the pyrolyzer includes secondary particles, such as airborne dust, fibers and dirt, and may also include biological agents, such as anthrax spores, bacterium or other particles containing biowarfare agents. A sample of the aerosolized particles is impacted at the bottom of a quartz tube (pyrotube) in the pyrolyzer. The air and residual particles that are not collected in the pyrotube are exhausted through an outlet.

During sample identification, the collected particle sample in the pyrotube is analyzed to identify any biological agents. A small droplet of a methylating reagent, such as tetramethylammonium hydroxide (TMAH) dissolved in methanol, is added to the particle sample in the pyrotube through a hypodermic needle. In one example, the hypodermic needle is made of stainless steel. If the sample includes any biological agents, the methylating reagent derivatizes organic materials to make them more volatile. For example, fatty acids in the cell walls of the bacterial agents form Fatty Acid Methylated Esters (FAMEs).

The sample in the pyrotube is then heated (pyrolyzed) to boil off the FAMES and other low volatile molecular fragments of the biological agents. A second pump draws 1 milliliter per minute of the gas molecules through the outlet and into a mass spectrometer for analysis and identification of any biological agents. Biological agents have a unique mixture of fatty acids and molecular fragments, known as bio-markers. If any biological agents are present in the sample, the mass spectrometer will produce a mass spectrum that indicates mass peaks for each of the bio-markers present. The bio-marker pattern is compared to a pre-programmed list of bio-markers produced by known biological agents to identify the biological agent in the air sample.

The pyrolyzer employs a single outlet line for both the air exhausted from the pyrolyzer during sample collection and the gas molecules directed to the mass spectrometer during sample analysis. The outlet line is a heated, stainless steel tube having a coating (for example, SilcoSteel) that renders the internal walls inert to chemicals.

The volume of gas released during pyrolysis is very small (typically one milliliter). The diameter of the outlet line must be relatively small to minimize the volume and provide fast delivery of the gas molecules to the mass spectrometer.

However, the small diameter (1 millimeter or less) of the outlet line increases the tendency of the outlet line to clog when the air that is exhausted contains a high level of background dust or fiber content.

The inert coating inside the outlet line is effective for transporting the gas molecules formed during pyrolysis, but is not effective in transporting the aerosol particles that are exhausted. The glass like inert coating is an insulator and causes the buildup of static electricity, which causes the aerosolized particles to stick to the inert coating. Over time, particles that coat the inside of the outlet line form chemically active sites that reduce the efficiency of the outlet line to transport the gas molecules to the mass spectrometer. The outlet line can also be periodically flushed with methanol and water to remove the active sites and/or can be replaced monthly. However, this is both laborious and costly.

Additionally, the methylating reagent is strongly basic and can break down the inert coating on the outlet line over time, again reducing the efficiency of the outlet line to transport bio-markers to the mass spectrometer. The outlet line is commonly replaced monthly to prevent this.

The prior art steel hypodermic needle that dispenses the methylating reagent solution also has drawbacks. For one, the needle is not reliable in delivering a consistent metered droplet of the methylating reagent solution, resulting in a lack of repeatability of the experiments. The compression fitting that feeds the needle through the walls of the pyrolyzer conducts heat to the needle, causing the temperature of the needle to increase above the boiling point of methanol and evaporating the methylating reagent solution passing through the needle. Additionally, repeated thermal cycling has been found to "age" the needle. The nickel in the stainless steel alloy can activate the surface and catalyze the break down of the FAMEs during pyrolysis.

Thus, it is desirable to have a dual-outlet pyrolyzer that can more effectively reduce clogging of the outlet line, as well as overcoming the other above-mentioned deficiencies of the prior art.

SUMMARY OF THE INVENTION

A pyrolyzer is part of a system that detects biological agents in the air. The pyrolyzer extracts particles from the air and derivitizes those particles with a methylating reagent. The pyrolyzer finally heats the derivitized products and other molecular fragments to form a gas mixture that can be analyzed by a mass spectrometer to determine the presence of chemicals (bio-markers) that indicate the presence of a biological warfare agent. The pyrolyzer includes an inlet and two outlet lines: an exhaust line for exhausting air drawn into the pyrolyzer during sample collection and a sample line for supplying the sample to the mass spectrometer during sample identification.

Each outlet is optimized to perform the required function. By separating the exhaust line and the sample line, particles are prevented from getting into and baking onto sidewalls of the sample line, which can form active sites that can block the transmission of bio-marker molecules to the mass spectrometer.

During sample collection, a sample pump draws air into the pyrolyzer through the inlet, and the aerosolized particles are impacted at the bottom of a quartz tube (pyrotube) in the pyrolyzer. The air and aerosol particles that are not collected in the pyrotube are exhausted from the pyrotube through the exhaust line. The exhaust line is electrically conducting and grounded to prevent electrostatic charge buildup and has a wide diameter to prevent clogging by particles and fibers.

After particle sample collection, a small droplet of a methylating reagent is added to the particle sample in the pyrotube. The methylating agent is added to the sample through a reagent line. The reagent line is a quartz capillary tube. If the sample includes any biological agents, the methylating reagent derivatizes organic materials to make them more volatile. For example, fatty acids in the cell walls of the bacterial agents form Fatty Acid Methylated Esters (FAMEs). The sample is then pyrolyzed, or heated, to form gas molecules.

The gas molecules are then drawn through the sample line and into the mass spectrometer by a sample pump for identification. The sample line is stainless steel and has an inert coating or a quartz capillary liner and a narrow diameter to provide timely transfer of the eluted gases from the pyrolyzer to the mass spectrometer. The mass spectrometer identifies any biological agents in the sample. The exhaust line is larger in diameter that the sample line to prevent clogging by airborne fibers and to permit a high flow rate.

These and other features of the present invention will be best understood from the following specification and drawings.

BRIEF DESCRIPTION OF THE DRAWINGS

The various features and advantages of the invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
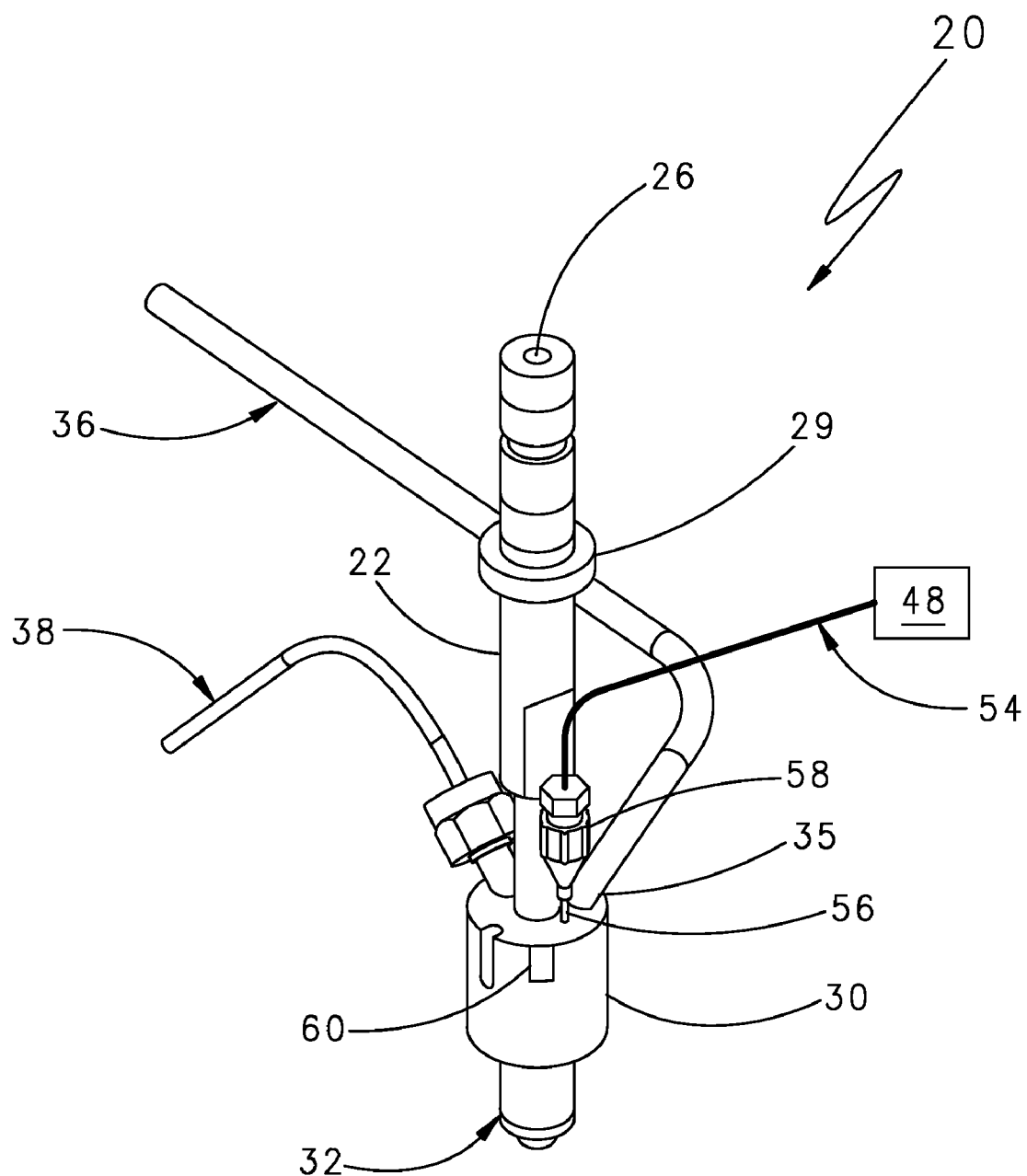
FIG. 1 illustrates a schematic perspective view of the dual outlet pyrolyzer of the present invention.
Figure 2:
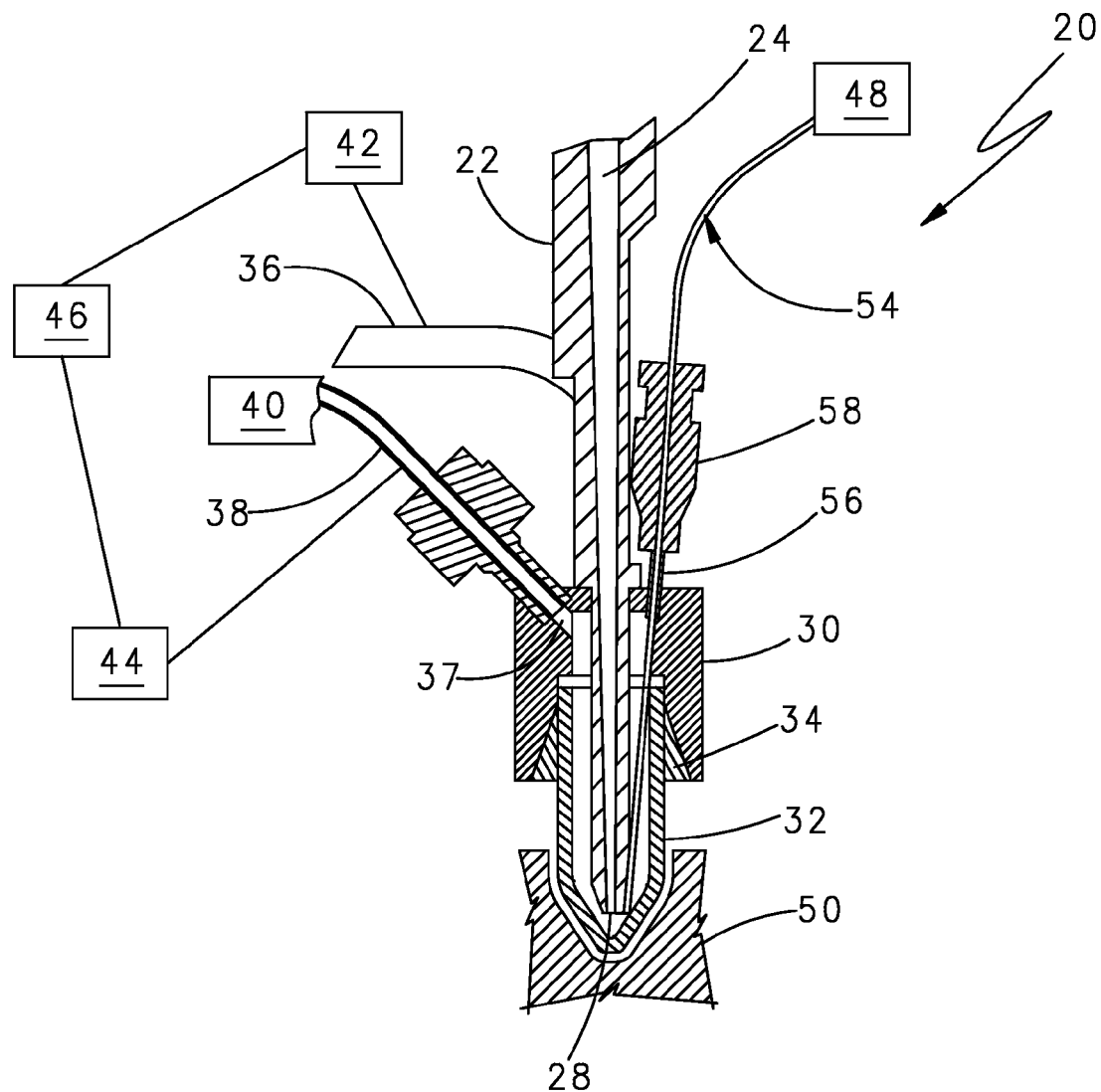
FIG. 2 illustrates a schematic cross-sectional front view of the dual outlet pyrolyzer of the present invention.

FIGS. 1 and 2 illustrate the pyrolyzer 20 of the present invention used to detect the presence of any biological agents, such as anthrax or other biological warfare agents, in a sample of air. The pyrolyzer 20 includes a body portion 22 having a passage 24 that extends through the body portion 22. Air enters the body portion 22 through an inlet 26 and exits the body portion 22 through an outlet 28. The passage 24 tapers from the inlet 26 to the outlet 28. A collar 29 attached to the body portion 22 of the pyrolyzer 20 allows the body portion 22 to be mounted to another structure. The body portion 22 is received in a pyrolyzer body 30 discussed below. The pyrolyzer 20 further includes a pyrotube 32 that collects the air sample drawn into pyrolyzer 20. A tube seal 34 around the pyrotube 32 provides sealing between the pyrotube 32 and the pyrolyzer body 30.

Air drawn into the pyrolyzer 20 through the inlet 26 is exhausted through an exhaust outlet 35. An exhaust line 36 is connected to the exhaust outlet 35. The internal surfaces of the exhaust line 36 are carefully polished and radiused to prevent fibers bridging and blocking the exhaust line 36. An exhaust pump 42 located on the exhaust line 36 creates a vacuum and draws air into the inlet 26 of the pyrolyzer 20.

A sample of gas produced in the pyrotube 32 during the pyrolysis (heater) phase travels through a sample outlet 37 to a mass spectrometer 40 for identification of any biological agents in the sample. A sample line 38 connects the sample outlet 37 to the mass spectrometer 40. A sample pump 44 draw the gas sample from the pyrolyzer 20 through the sample line 38. A "T" connection is formed at the location where the sample pump 44 joins the sample line 38. As the gas sample passes through the sample line 38, a portion enters the mass spectrometer 40 for analysis. The pyrolyzer body 30 supports the exhaust line 36 and the sample line 38.

During sample collection, the exhaust pump 42 draws 1 liter of air per minute through the exhaust line 36 for exhausting to the atmosphere. This creates a low pressure internal to the pyrolyzer tube, causing a sample of air to enter at the inlet 26 of the pyrolyzer 20 and be drawn into the passage 24 of the pyrolyzer 20. The internal taper of the passage 24 increases the velocity of the airflow through the passage 24. The high velocity air that emerges from the passage 24 at the outlet 28 is directed at the bottom of the pyrotube 32. Any dust particles containing bacterial agents, bacterium or spores that are carried by the air will impact the bottom of the pyrotube 32 and stick to the surface. During sample collection, the exhaust pump 42 is on and the sample pump 44 is off. The duration of the sample collection is programmable by software. In one example, the sample is collected for 1 to 5 minutes. One skilled in the art would know how long to collect the sample. After sample collection is complete, a control 46 turns the exhaust pump 42 off.

The exhaust outlet 35 and the exhaust line 36 are made of electrically conducting material, such as stainless steel, and are not coated. The electrical conductivity is required to prevent buildup of static electricity so that aerosol dust and fibers will not be attracted to the walls, preventing clogging of the exhaust outlet 35 and the exhaust line 36. If any exhausted particles do stick to the exhaust line 36, the analytical performance of the mass spectrometer 40 is not affected because the exhaust line 36 is not used to transport the sample to be identified to the mass spectrometer 40.

In the second step, any biological agents in the sample in the pyrotube 32 are analyzed and identified. A small droplet (1 to 2 microliters) of a methylating reagent, such as 0.015 to 0.0015 Molar tetramethylammonium hydroxide (TMAH) dissolved in methanol, is added to the sample in the pyrotube 32 through a reagent line 54 from a reagent source 48. The reagent line 54 is also supported by the pyrolyzer body 30. If the sample includes any biological agents, the methylating reagent derivatizes organic materials to make them more volatile. For example, fatty acids in the cell walls of the bacterial agents form Fatty Acid Methylated Esters (FAMEs).

The reagent line 54 is a fused straight quartz capillary tube having an inner diameter of approximately 150 micrometers. The quartz capillary tube is an inert material that resists the strongly basic methylating reagent and is unaffected by thermal cycling. The relatively large inner diameter lowers the conductance and in turn increases the delivery velocity. This reduces the contact time between the methylating reagent solution and the hot capillary walls as the methylating reagent transits through the pyrolyzer body 30 to the pyrotube 32. The reagent line 54 extends directly into the bottom of the pyrotube 32. The size of the methylating reagent droplet provided from the reagent source 48 is consistent and repeatable.

A thermal break 56 located at the entry point of the reagent line 54 in the pyrolyzer 20 reduces the flow of heat to the reagent line 54. The thermal break 56 is a section of thin wall stainless steel tubing (approximately 1/32" in diameter) having high thermal impedance that connects a compression fitting 58 to the pyrolyzer body 30. The pyrolyzer body 30 is hot (approximately 230° C.), and the thermal break 56 keeps the compression fitting 58 cool. The compression fitting 58 seals the reagent line 54 at the point of entry to the pyrolyzer body 30 and is thermally connected to an unheated (ambient temperature) location to prevent thermal conduction to the reagent line 54. The compression fitting 58 is therefore maintained at a temperature less than 65° C., or the boiling point of methanol. A temperature sensor 60 detects the temperature of the pyrolyzer body 30. If the temperature sensor 60 detects that the temperature of the pyrolyzer body 30 drops below 230° C., a heater (not shown) heats the pyrolyzer body 30 to maintain the temperature at 230° C.

After collecting, the sample in the pyrotube 32 is then pyrolyzed, or heated, by a heater 50 to form gas molecules. The sample can be pyrolyzed for approximately 5 seconds to 20 seconds. However, one skilled in the art would know how long to pyrolyze the sample collected in the pyrotube 32.

The control 46 turns the sample pump 44 on to direct the sample in the pyrotube 32 to the mass spectrometer 40. The sample pump 44 draws 1 milliliter per minute of the gas molecules in the pyrotube 32 through the sample line 38 and into the mass spectrometer 40 for analysis.

The sample line 38 is a heated, stainless steel tube having a fused quartz capillary tubing lining. The stainless steel tube provides mechanical protection for the fragile quartz capillary lining. The quartz lining is chemically inert and resistant to the methylating reagent solution and extends through the outlet 37 and into the headspace above the pyrotube 32 or down inside the pyrotube 32. The FAMEs are generally eluted at the bottom of the pyrotube 32, and a sample of the FAMEs from the bottom of the pyrotube 32 can be drawn to provide a more concentrated sample to improve accuracy.

The diameter of the sample line 38 is small to provide relatively fast sample delivery to the mass spectrometer 40. Preferably, the inner diameter of the sample line 38 is approximately 0.006 of an inch. Quickly detachable access covers permit the quartz lining to be easily removed and replaced. Alternately, the sample line 38 has a SilcoSteel coating with an inner diameter of approximately 0.040 of an inch.

Each specific biological agent, when processed by the pyrolyzer 20, will produce a gas mixture containing a mix of chemicals (bio-markers), such as Fatty Acid Methylated Esters (FAMEs) and other organic molecule fragments, that uniquely identify that agent. The mass spectrometer 40 includes a preprogrammed list of bio-markers for each biological agent to be detected. If any biological agents are present the sample, the mass spectrometer 40 identifies the biological agents by comparing the identified bio-marker pattern to the list of bio-marker patterns preprogrammed into the mass spectrometer 40. After a match is found, the mass spectrometer 40 identifies the associated biological agent.

The flow through the exhaust line 36 is approximately one thousand times greater than the flow through the sample line 38 (one liter per minute of exhaust flows through the exhaust line 36 versus 1 millimeter per minute of gas molecules flow through the sample line 38). The exhaust line 36 of the present invention has a larger diameter than the diameter of the sample line 38 to accommodate the greater flow of exhaust air through the exhaust line 36 than the sample line 38. The exhaust line 36 is dedicated to aerosol sample transport and collection, and the sample line 38 is dedicated to transport of gases generated during pyrolysis. Therefore, the mode valve of the prior art is not required. Providing an exhaust line 36 that is independent of the sample line 38 allows the pyrotube 32 to be heated to a high temperature (500° C.) for bakeout (cleaning), without risk of the low volatile gaseous products contaminating the sample line 38. During bakeout, the exhaust pump 42 is turned on and the sample pump 44 is turned off to prevent gases from entering the sample path 38.

The pyrolyzer 20 of the present invention can be used to detect biological agents used in biological warfare, such as anthrax. However, it is to be understood that other biological agents can be detected. Any substance having a unique pattern of fatty acids or other chemicals that can be identified by a mass spectrometer 40 can be detected and identified.

The foregoing description is only exemplary of the principles of the invention. Many modifications and variations of the present invention are possible in light of the above teachings. The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described. For that reason the following claims should be studied to determine the true scope and content of this invention.

What is claimed is:

1. A biological agent detection system comprising:
   a pyrolyzer including a tube for collecting and processing a particle sample;
   an inlet for fluid communication with the tube for drawing air containing the particle sample into the pyrolyzer;
   a first outlet for fluid communication with an exhaust to exhaust the air from the pyrolyzer to atmosphere; and
   a second outlet for fluid communication with a mass spectrometer, wherein gas molecules eluted from the particle sample collected and processed in the tube are drawn into the mass spectrometer through the second outlet for identification.

2. The detection system as recited in claim 1 further including a first pump that draws the air into the pyrolyzer through the inlet and out of the pyrolyzer through the first outlet and a second pump that draws the gas molecules from the tube into the mass spectrometer.

3. The detection system as recited in claim 2 wherein the first pump is active and the second pump is inactive during collection of the particle sample in the tube.

4. The detection system as recited in claim 2 wherein the first pump is inactive and the second pump is active when the gas molecules from the tube are drawn through the second outlet and into the mass spectrometer.

5. The detection system as recited in claim 2 further including a control for activating and deactivating the first pump and the second pump.

6. The detection system as recited in claim 2 further including a first line interconnecting the first outlet to the exhaust and a second line interconnecting the second outlet to the mass spectrometer, wherein the first line has a greater diameter than the second line.

7. The detection system as recited in claim 6 wherein the first pump is operably coupled to the first line and the second pump is operably coupled to the second line.

8. The detection system as recited in claim 6 wherein the second line is a stainless steel tube with a quartz lining.

9. The detection system as recited in claim 1 further including a reagent source containing a methylating reagent, wherein the methylating reagent is added to the particle sample collected in the tube through a reagent line to derivatize the particle sample into volatile pyrolysis products.

10. The detection system as recited in claim 9 further including a heater to pyrolyze the volatile pyrolysis products into the gas molecules.

11. The detection system as recited in claim 9 wherein the reagent line is quartz.

12. The detection system as recited in claim 9 wherein the reagent line is aligned with a bottom of the tube to precisely deliver the methylating reagent to the particle sample at the bottom of the tube.

13. The detection system as recited in claim 9 wherein the reagent line includes a thermal break that minimizes heat transfer from the pyrolyzer to the methylating reagent as the methylating reagent flows through the reagent line.

14. The detection system as recited in claim 1 wherein the air includes secondary particles and biological agents.

15. A biological agent detection system comprising:
a pyrolyzer including a tube for collecting and processing a particle sample;
a mass spectrometer for identifying biological agents in the particle sample;
an inlet in fluid communication with the tube for drawing air containing the particle sample into the pyrolyzer;
a first outlet in fluid communication with an exhaust to exhaust the air from the pyrolyzer to atmosphere;
a second outlet in fluid communication with the mass spectrometer, wherein gas molecules eluted from the particle sample collected and processed in the tube are drawn into the mass spectrometer through the second outlet for identification;
a reagent source containing a methylating reagent, wherein the methylating agent is added to the particle sample collected in the tube to derivatize the particle sample;
a heater to pyrolyze the particle sample that is derivatized;
a first pump for drawing the air into the pyrolyzer through the inlet and out of the pyrolyzer through the first outlet; and
a second pump for drawing the gas molecules from the tube into the mass spectrometer through the second outlet.

16. The detection system as recited in claim 15 wherein the first pump is active and the second pump is inactive during collection of the sample in the tube and the second pump is active and the first pump is inactive when the gas molecules from the tube is drawn through the second outlet.

17. The detection system as recited in claim 15 further including a first line interconnecting the first outlet to the exhaust and a second line interconnecting the second outlet to the mass spectrometer, wherein the first line has a greater diameter than the second line.

18. The detecting system as recited in claim 17 wherein the second line is a stainless steel tube with a quartz lining.

19. The detecting system as recited in claim 15 wherein the methylating agent is added to the sample collected in the tube from the reagent source through a reagent line, and the reagent line is made of quartz.

20. A method for detecting a biological agent, the method comprising the steps of:
drawing air into a pyrolyzer through an inlet in communication with a tube of the pyrolyzer;
exhausting the air through a first outlet of the pyrolyzer in fluid communication with an exhaust to atmosphere;
collecting a particle sample in the tube;
adding a methylating reagent to the particle sample in the tube to derivatize the particle sample in the tube;
pyrolyzing the particle sample to form gas molecules;
drawing the gas molecules through a second outlet in fluid communication and into a mass spectrometer; and
identifying any biological agents in the particle sample.

21. The detection system as recited in claim 1 wherein the first outlet and the second outlet are separate.

22. The detection system as recited in claim 15 wherein the first outlet and the second outlet are separate.

* * * * *